(12) United States Patent
Bratkovski et al.

(10) Patent No.: US 8,670,119 B1
(45) Date of Patent: Mar. 11, 2014

(54) APPARATUS HAVING SURFACE-ENHANCED SPECTROSCOPY MODULES

(71) Applicant: Hewlett-Packard Development Company, L.P., Houston, TX (US)

(72) Inventors: Alexandre M Bratkovski, Mountain View, CA (US); Zhiyong Li, Foster City, CA (US); Gary Gibson, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 13/754,456

(22) Filed: Jan. 30, 2013

(51) Int. Cl.
*G01J 3/44* (2006.01)

(52) U.S. Cl.
USPC ............................................. 356/301

(58) Field of Classification Search
USPC ............................................. 356/301, 72–73
See application file for complete search history.

(56) References Cited

U.S. PATENT DOCUMENTS

| 6,975,891 | B2 | 12/2005 | Pawluczyk |
| 2002/0126289 | A1 | 9/2002 | Marquardt et al. |
| 2012/0242987 | A1* | 9/2012 | Liu et al. ................. 356/301 |

FOREIGN PATENT DOCUMENTS

CN 101248085 8/2008

* cited by examiner

*Primary Examiner* — Tarifur Chodwhury
*Assistant Examiner* — Abdullah Nur

(57) ABSTRACT

According to an example, an apparatus for performing spectroscopy includes a perimeter wall extending between a first end and a second end of the perimeter wall along a first axis, in which an interior surface of the perimeter wall forms a hollow core extending along the first axis. The perimeter wall has openings at both the first end and the second end and light is to pass through the perimeter wall. The apparatus also includes a plurality of SES modules positioned around an inner circumference of the perimeter wall in a spaced arrangement with respect to each other to allow light to enter into the hollow core in gaps between the plurality of SES modules, in which each of the plurality of SES modules is positioned substantially across from a gap.

20 Claims, 6 Drawing Sheets

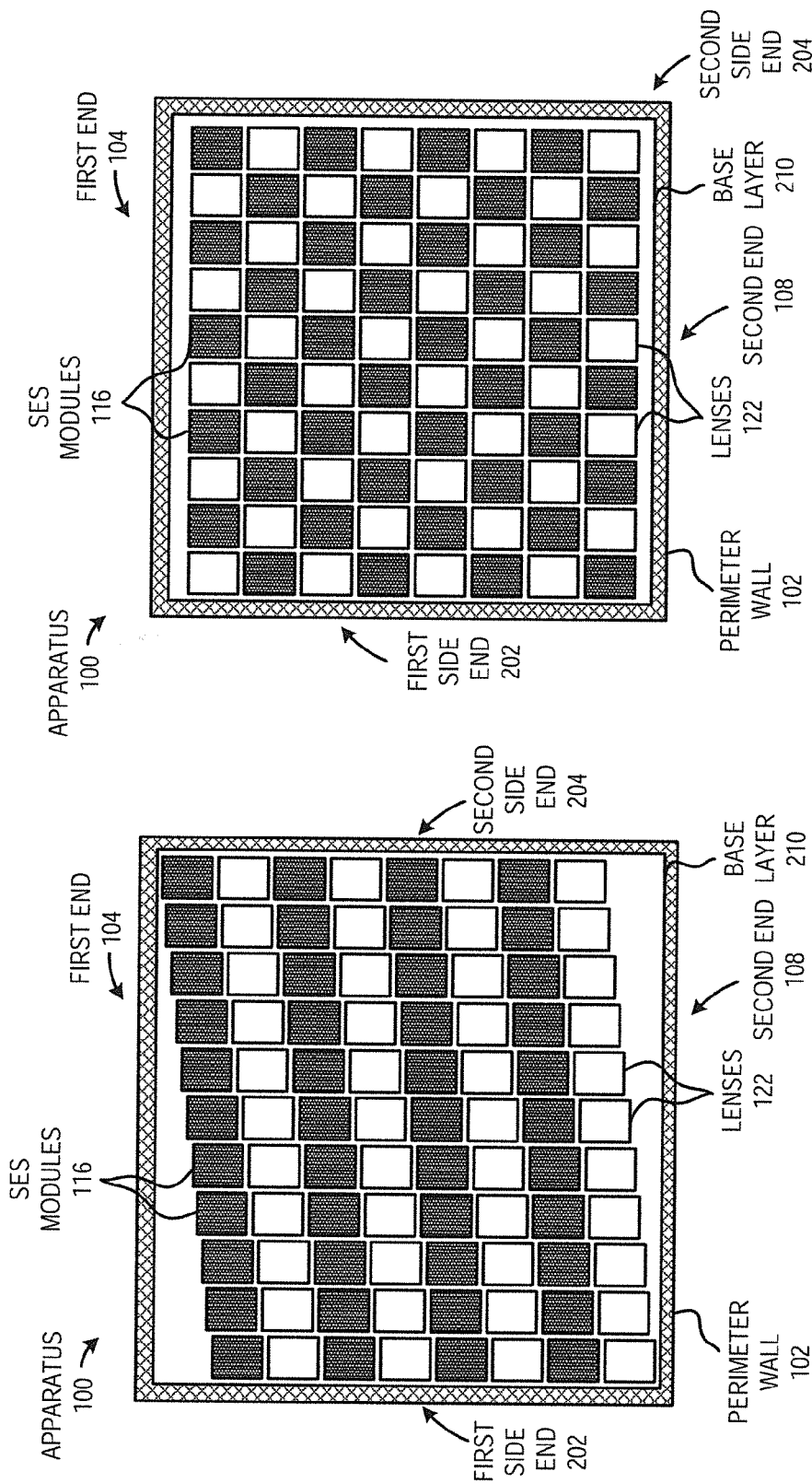

APPARATUS HAVING SURFACE-ENHANCED SPECTROSCOPY MODULES

BACKGROUND

In surface-enhanced spectroscopy (SES), such as surface-enhanced Raman spectroscopy (SERS), vibrationally excitable levels of an analyte are probed. The energy of a photon can shift by an amount equal to that of the vibrational level excited by the photon (Raman scattering). A Raman spectrum, which consists of a wavelength distribution of bands corresponding to molecular vibrations specific to the analyte being probed, may be detected to identify the analyte. In SERS, the analyte molecules are in contact or close proximity, for instance, less than ten nanometers, to metal nano-particles that may be or may not be coated with a dielectric, such as silicon dioxide, silicon nitride, and a polymer, that, once excited by light, support plasmon modes (collective oscillations of free electron density), which create strong near fields around the metal nano-particles. These fields can couple to analyte molecules in the near field regions, enhancing the Raman scattering from the analyte molecules.

SERS has recently been performed to probe fluids in a specimen in vivo through implantation of the metal nano-particles subcutaneously. However, conventional devices on which SERS is performed typically include an asymmetric arrangement of the metal nano-particles in the active detecting region and thus, problems with orientation often arise with their use due to the likelihood of them being misoriented.

BRIEF DESCRIPTION OF THE DRAWINGS

Features of the present disclosure are illustrated by way of example and not limited in the following figure(s), in which like numerals indicate like elements, in which:

FIGS. 2A and 2B, respectively show diagrams of the apparatus 100 respectively depicted in FIGS. 1B and 1D, according to two examples of the present disclosure;

DETAILED DESCRIPTION

Figure 1B:
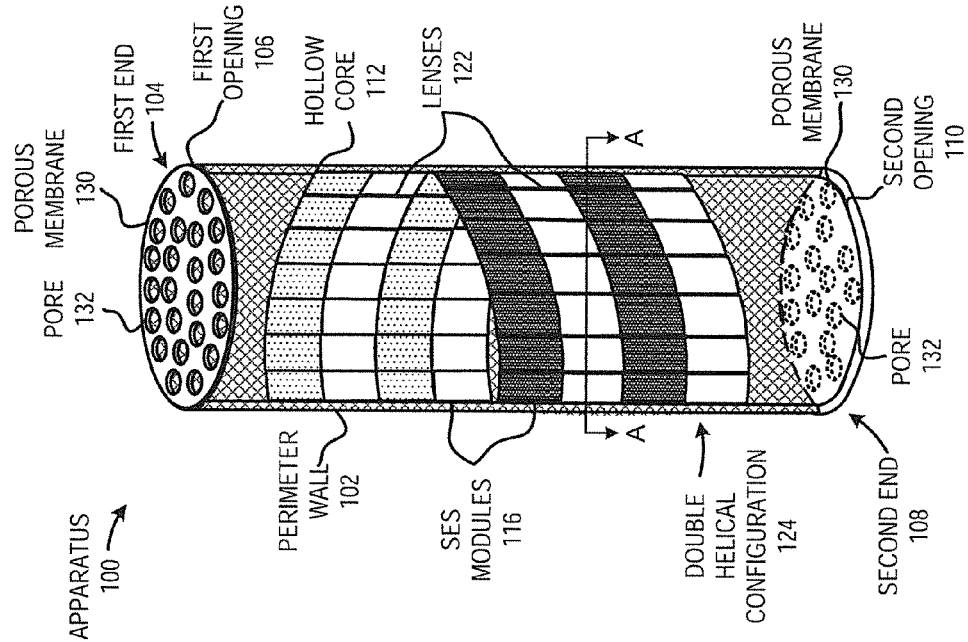
FIG. 1B shows a simplified, partially cut away, perspective view of an apparatus for performing spectroscopy, according to another example of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared, near infrared, and ultra-violet portions of the electromagnetic spectrum.

Disclosed herein are apparatuses for performing spectroscopy, systems for performing surface-enhanced spectroscopy (SES), and methods for fabricating an apparatuses. The apparatuses disclosed herein may include a perimeter wall extending between a first end and a second end of the perimeter wall along a first axis, in which an interior surface of the perimeter wall may form a hollow core extending along the first axis. The perimeter wall may have openings at both the first end and the second end and light may pass through the perimeter wall. The apparatus may also include a plurality of SES modules positioned around an inner circumference of the perimeter wall in a spaced arrangement with respect to each other to allow light to enter into the hollow core in gaps between the SES modules, and each of the SES modules may be positioned substantially across from a gap.

According to an example, a plurality of lenses may be positioned in a plurality of gaps between the SES modules. The lenses may have lengths and widths that are similar to the lengths and widths of the SES modules. Alternatively, however, the lenses may have different lengths and widths as compared with the SES modules. In any regard, the lenses may be focusing lenses that may enhance intensities of light being directed onto the SES modules. Alternatively, the lenses may be non-focusing and may thus be provided in the apparatus to maintain gaps between the SES modules.

The SES modules, and if included, the lenses, may be positioned in a pattern that is substantially symmetrical about multiple planes along a central longitudinal axis of the apparatus. The pattern of SES modules is substantially symmetrical because there may be some slight deviations among the SES modules and/or the positions at which the SES modules are located on the perimeter wall. By way of particular example, an apparatus having deviations in the SES modules and/or the positions of the SES modules on opposite sides of the plane of about 10% or less may be construed as being substantially symmetrical.

The substantial symmetry of the SES modules about a plane along a central longitudinal axis of the apparatus along with the positioning of the gaps between the SES modules may enable light to be directed onto a SES module regardless of which section of the apparatus light is directed. As such, if the orientation of the apparatus changes following implantation of the apparatus into a specimen, for instance, the apparatus rotates about its central longitudinal axis, the apparatus may still be used for performing spectroscopy. In contrast, conventional apparatuses are designed to assume a particular orientation with regard to a reader device/radiation source. As such, conventional apparatuses may be rendered non-functional if the conventional apparatuses are not in the correct orientation.

Figure 1A:
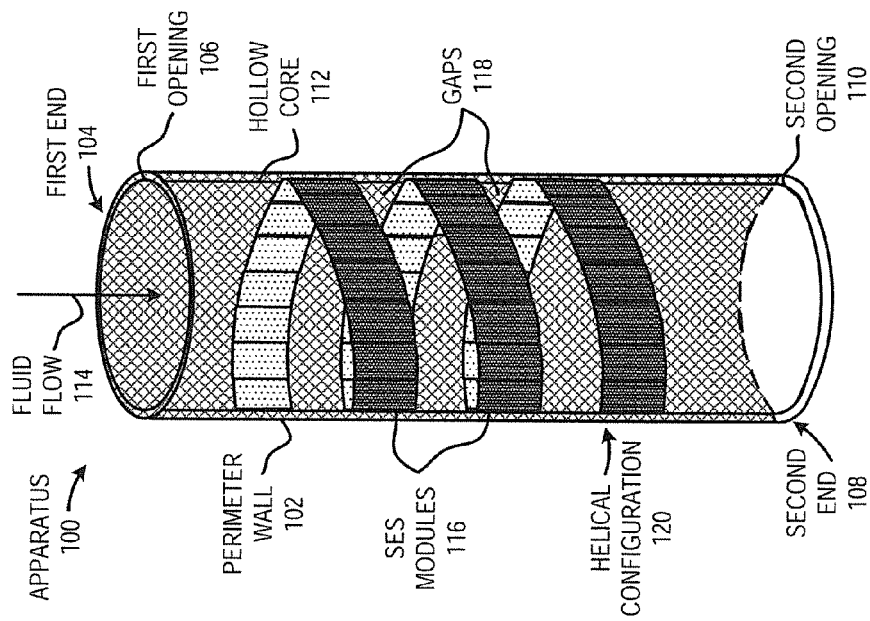
FIG. 1A shows a simplified, partially cut away, perspective view of an apparatus for performing spectroscopy, according to an example of the present disclosure.

With reference first to FIG. 1A, there is shown a simplified, partially cut away, perspective view of an apparatus 100 for performing spectroscopy, according to an example. It should be understood that the apparatus 100 depicted in FIG. 1A may include additional components and that some of the components described herein may be removed and/or modified without departing from a scope of the apparatus 100. It should also be understood that the components depicted in FIG. 1A are not drawn to scale and thus, the components may have different relative sizes with respect to each other than as shown therein.

The apparatus 100 may be implemented to perform spectroscopy (also referred herein as surface-enhanced spectroscopy (SES), which may include surface-enhanced Raman spectroscopy (SERS), surface-enhanced luminescence detection, surface-enhanced fluorescence detection, or other types of surface-enhanced optically enhanced detection, to detect a molecule in an analyte sample with a relatively high level of sensitivity. The apparatus 100 may have a size, a configuration, and may be fabricated of materials that make the apparatus 100 suitable for implantation into a specimen. As a particular example, the apparatus 100 may be implemented to perform spectroscopy in vivo, i.e., following implantation of the apparatus 100 into a specimen, such as a human, an animal, an insect, a plant, non-living item, etc. The apparatus 100 may thus be implemented to analyze molecules in a fluid specimen, such as blood, lymph, saliva, interstitial fluid, etc. The apparatus 100 may alternatively be implemented in spectroscopy applications that do not involve implantation of the apparatus 100.

As shown, the apparatus 100 includes a perimeter wall 102, which may extend from a first end 104 to a second end 108 along a first axis. The first end 104 is depicted as including a first opening 106 and the second end 108 is depicted as including a second opening 110. The perimeter wall 102 is also depicted as having a hollow core 112 formed by the interior surface of the perimeter wall 102. In this regard, fluid that may include analyte molecules to be spectrally analyzed may flow into the hollow core 112, for instance, as denoted by the arrow 114.

The perimeter wall 102 may be formed of any material suitable for implantation into a specimen, such as silicon, polymer, plastic, silver, titanium, etc. The perimeter wall 102 may also be formed of other materials, such as materials that may be toxic to a specimen, in instances where the apparatus 100 is to be implemented without being implanted into a specimen. In addition, the perimeter wall 102 may be formed of an optically transparent material and/or with a plurality of holes, for instance, as a mesh structure, to enable light to pass through a perimeter wall of the perimeter wall 102. Particularly, the perimeter wall 102 may be formed of a material and/or a configuration that enables a sufficient intensity of an illumination beam to pass through the perimeter wall 102 for light, e.g., Raman scattered light, fluorescence, luminescence, etc., to be emitted from analyte molecules contained inside of the apparatus 100 and for the emitted light to be of sufficient intensity to exit from the apparatus 100 and be detected.

A front portion of the perimeter wall 102 has been cut away from FIG. 1A to enable an interior of the perimeter wall 102 and the components contained therein to be visible. As shown, a plurality of SES modules 116 are depicted as being positioned around an inner circumference of the perimeter wall 102 in a spaced arrangement with respect to each other to allow light to enter into the hollow core 112 through gaps 118 between the SES modules 116. Particularly, each of the SES modules 116 may be positioned substantially across from a gap 118 with respect to the circumference of the perimeter wall 102, such that light passing through a gap 118 may be likely to be directed onto a SES module 116 located across from the gap 118. In addition, the SES modules 116 are depicted as being arranged in a helical configuration 120. The helical configuration 120 may also be considered as a spiral configuration.

According to an example, the SES modules 116 may be arranged in the helical configuration 120 at a predetermined angle that enables light entering into the hollow core 112 substantially perpendicularly through the gaps 118 to be directed to a SES module 116 or SES modules positioned on an opposite side of the gaps 118 in the hollow core 102 through which the light entered into the hollow core 112. For instance, each revolution of the SES modules 116 around the perimeter wall 102 may be shifted by one period. In other words, the SES modules 116 and the gaps 118 may be arranged in the interior surface of the perimeter wall 102 such that a SES module 116 is positioned substantially directly across from a gap 118 around the circumference of the perimeter wall 102. According to an example in which the perimeter wall 102 may have a spherical cross-section, each of the SES modules 116 may be positioned at approximately 180° around the circumference of the perimeter wall 102 from an opposing gap 118.

In one regard, therefore, the SES modules 116 may be positioned in a pattern that is substantially symmetrical about multiple planes along a central longitudinal axis of the perimeter wall 102, i.e., substantially symmetrical about multiple planes that extend centrally from the first end 104 to the second end 108. In addition, this substantial symmetry may be maintained regardless of the angle of the plane around the central longitudinal axis of the perimeter wall 102. As such, regardless of the direction in which light enters into the apparatus 100, there is a relatively high degree of likelihood that the light will be directed onto a SES module 116. In addition, light, such as Raman scattered light, fluorescence, luminescence, etc., emitted by molecules near the SES elements 116 may also exit out of the perimeter wall 102 through a gap 118.

According to an example, the apparatus 100 may be a surgically implantable stent. As such, the perimeter wall 102 may have a maximum diameter that is between about 1 mm and about 5 mm and a length that is between about 0.5 cm to about 2 cm. In addition, the SES modules 116 may have widths that enable a plurality of the SES modules 116 to be positioned along the perimeter wall 102, for instance, about 20-40 SES modules 116 per revolution around the perimeter wall 102. By way of example, each of the SES elements 116 may have lengths and widths that are between about 5 microns to about 500 microns.

Generally speaking, the SES modules 116 may include substrates on which a plurality of SES elements (for instance, SES elements 406 depicted in FIG. 4A) may be provided in a substantially ordered or random arrangement. The SES elements may include any suitable structures and/or configurations that enhance Raman scattering and/or other types of non-Raman light emissions from analytes positioned on or near the SES elements. By way of example, Raman-enhancing elements may include plasmonic nano-particles or other Raman-enhancing structures. The Raman-enhancing elements may one or both of enhance Raman scattering and facilitate analyte adsorption. The SES elements may be nanoparticles or other structures that additionally or alternatively enhance photoluminescence, fluorescence, etc.

The SES elements may be plasmonic nanoparticles or nanostructures, which may be plasmon-supporting materials such as but not limited to, gold (Au), silver (Ag), and copper (Cu). The SES elements may have nanoscale surface roughness, which is generally characterized by nanoscale surface features on the surface of the layer(s) and may be produced spontaneously during deposition of the plasmon-supporting material layer(s). By definition herein, a plasmon-supporting material may be a material that facilitates Raman scattering and/or non-Raman light emission from an analyte on or near the material during Raman spectroscopy.

In some examples, the SES elements of the SES modules 116 may be functionalized to facilitate adsorption of analyte molecules. For example, surfaces of the SES elements may be functionalized such that a particular class of analytes is attracted and may bond or be preferentially adsorbed onto the SES elements. Various manners in which the SES elements may operate to enhance Raman scattered light and/or non-Raman light emissions from analyte molecules are described in greater detail herein below.

With reference now to FIG. 1B, there is shown a simplified perspective view of the apparatus 100 depicted in FIG. 1B, according to another example. The apparatus 100 depicted in FIG. 1B includes all of the same features as those depicted in FIG. 1A and thus, common features will not be described again with respect to FIG. 1B. The apparatus 100 depicted in FIG. 1B differs from the apparatus 100 depicted in FIG. 1A in that the apparatus 100 may include lenses 122 in place of the gaps 118. According to an example, the lenses 122 have similar widths and lengths as the SES modules 116.

As shown in FIG. 1B, like the SES modules 116, the lenses 122 are arranged in a helical configuration. Particularly, the SES modules 116 and the lenses 122 are depicted as being arranged in a double helical configuration 124, in which the SES modules 116 may form a first part of the double helical configuration 124 and the lenses 122 may form the second part of the double helical configuration 124. The double helical configuration 124 may also be considered as a double spiral configuration, in which the SES modules 116 and the lenses 122 may extend from near the second end 108 to near the first end 104. Portions of the SES modules 116 and the lenses 122 have been cut away from FIG. 1B to enable the opposite surfaces of the SES modules 116 and the lenses 122 to be visible. It should therefore be understood that the SES modules 116 and the lenses 122 may extend between near the second end 108 and near the first end 104.

According to an example, the SES modules 116 and the lenses 122 may be arranged in the double helical configuration 124 at a predetermined angle that enables light entering into the hollow core 112 substantially perpendicularly to the lenses 122 to be directed to a respective SES module 116 positioned on an opposite side of the hollow core 112. For instance, each revolution of the SES modules 116 and the lenses 122 around the perimeter wall 102 may be shifted by one period. In other words, the SES modules 116 and the lenses 122 may be arranged in the interior surface of the perimeter wall 102 such that a SES module 116 is positioned substantially directly across a lens 122 around the circumference of the perimeter wall 102. According to an example in which the perimeter wall 102 may have a spherical cross-section, each of the SES modules 116 may be positioned at approximately 180° around the circumference of the perimeter wall 102 from an opposing lens 122.

In one regard, therefore, the SES modules 116 and the lenses 122 may be positioned in a pattern that is substantially symmetrical about multiple planes along a central longitudinal axis of the perimeter wall 102, which extends from the first end 104 to the second end 108. In addition, this symmetry may be maintained regardless of the angle of the plane around the central longitudinal axis of the perimeter wall 102. As such, regardless of the direction in which light enters into the apparatus 100, there is a relatively high degree of likelihood that the light will be directed onto a SES module 116. In addition, light, such as Raman scattered light, fluorescence, luminescence, etc., emitted by molecules near the SES modules 116 may also exit the perimeter wall 102 through a lens 122.

The apparatus 100 in FIG. 1B is also depicted as including porous membranes 130 having pores 132 on the first opening 106 and the second opening 110. One or both of the porous membranes 130 may, however, be omitted from the apparatus 100 in other examples. In addition, the porous membrane(s) 130 may equivalently be provided at the first end 104 and/or the second end 108 of the apparatus 100 depicted in FIG. 1A.

A first porous membrane 130 may span and cover the first opening 106 and a second porous membrane 130 may span and cover the second opening 110, such that a fluid may be required to pass through at least one of the porous membranes 130 to enter into the hollow core 112. In this regard, the porous membranes 130 may substantially block various materials from entering into the hollow core 112 and therefore filter the fluid entering into the hollow core 112. In addition, therefore, only molecules having a sufficiently small size to fit through the pores 132 may be able to enter into the hollow core 112. The pores 132 may also have particular shapes to enable selective entry of molecules having particular shapes. In addition, or alternatively, the porous membranes 130 may be functionalized with receptors of molecules that are not expected to pass through the pores 132. In this example, the porous membranes 130 may be functionalized with receptors of various types of molecules so that multiple species in the fluid may be selectively and efficiently blocked.

The porous membranes 130 may also be formed to enable light, including excitation light and light emitted/scattered from analyte molecules inside the hollow core 112 to substantially pass therethrough. In this example, the porous membranes 130 may be formed with pores 132 having a sufficiently thin size and/or formed of an optically transparent material to enable the light to pass therethrough. By way of particular example, the porous membranes 130 may have thicknesses that are between about 10 nm to about 100 nm. Additionally, although the porous membranes 130 have been depicted as having a relatively thin configuration, the porous membranes 130 may alternatively have a thicker, sponge-like, configuration.

The porous membranes 130 may be held in position over the respective openings 106 and 110 through use of, for instance, medical grade glue, or other biocompatible adhesives. In addition, the porous membranes 130 may be composed of any suitable material that enables the porous membranes 130 to perform the functions in the apparatus 100 discussed herein. Examples of suitable materials for the porous membranes 130 may include cellulose acetate, urethane based polymer (for example, polyurethane, polyether urethane, or polycarbonate urethane), ethylene glycol based polymer, heparin-functionalized polymer, a combination of these materials, etc.

By way of example, the pores 132 may be fabricated into the porous membrane(s) 130 through implementation of a molecular imprinting technique. In this technique, for instance, molecules that are to be allowed to pass through the porous membrane(s) 130 may be mixed with a polymer material and the mixture may be formed into a relatively thin sheet and resist cured, e.g., UV cured. The molecule may then be dissolved from the relatively thin sheet of mixed material, thereby leaving pores that are specially shaped to the molecules that may be allowed to pass through the porous membrane(s) 130. The thin sheet of material may then be positioned on a supporting porous sub-layer (not shown) and the combined layers may be positioned over the opening 108 and attached to the perimeter wall 102.

According to another example, each of the porous membranes 130 may be a lipid bilayer, which is a thin polar membrane made of two layers of lipid molecules. The lipid bilayer may include relatively flat sheets of lipid molecules that form a continuous barrier around cells. The lipid bilayer includes proteins that serve as transporting vehicles through the lipid bilayer membrane. In this regard, the proteins may selectively transport molecules, for instance, molecules having sufficiently small sizes to pass through the lipid bilayer membrane, through the lipid bilayer membrane, which therefore enables the lipid bilayer membrane to operate as a filter. The lipid bilayer may be collected from naturally occurring cells and/or fabricated synthetically from lipid molecules. In any regard, the lipid bilayer may be positioned, for instance, by coating the lipid bilayer on a supporting porous sub-layer (not shown) and the combined layers may be positioned over the openings 106 and 110 and attached to the perimeter wall 102.

According to a further example, the porous membrane(s) 130 may be functionalized to include host molecules, such as crown ethers, cyclodextrins, etc., that are to bond to corresponding guest molecules. Because the molecules corresponding to the host molecules bond to the host molecules, the corresponding guest molecules may substantially be prevented from entering into the hollow core 112 through the porous membrane(s) 130.

Figure 1D:
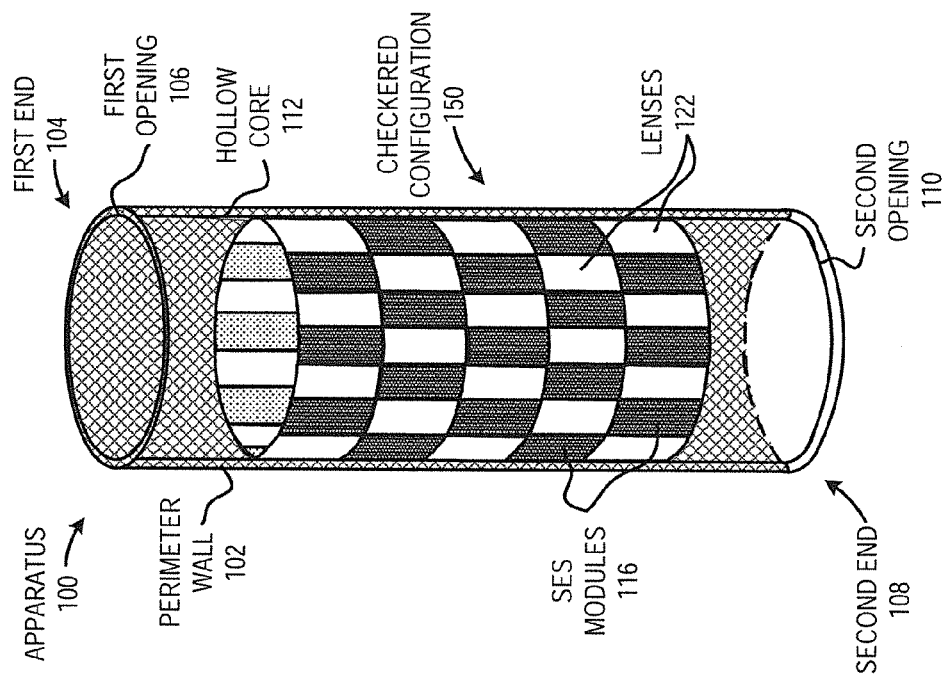
FIG. 1D shows a simplified perspective view of the apparatus depicted in FIGS. 1A and 1B, according to another example of the present disclosure.
Figure 1C:
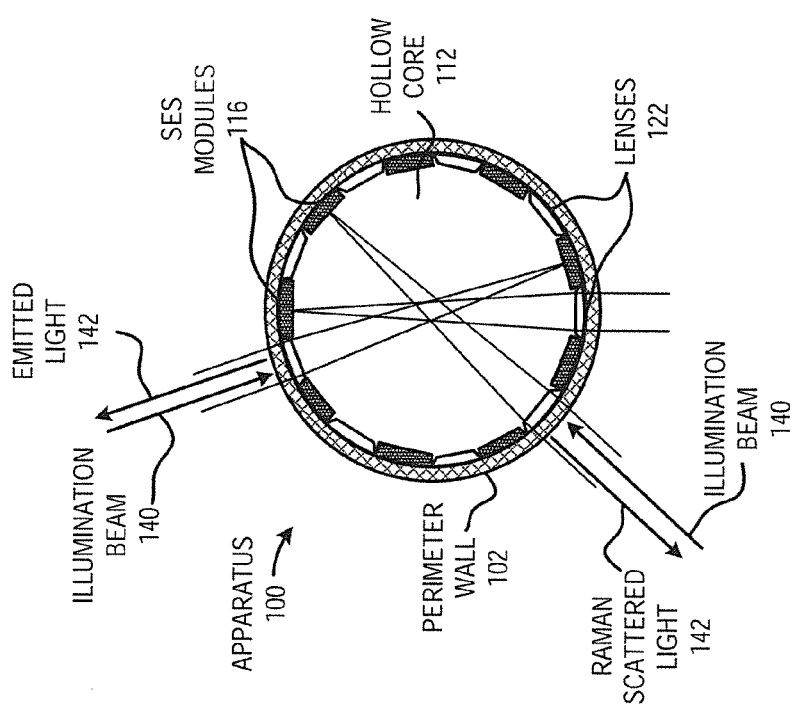
FIG. 1C shows an enlarged, cross-sectional view of the apparatus depicted in FIG. 1B taken along lines A-A, according to an example of the present disclosure.

Turning now to FIG. 1C, there is shown an enlarged, cross-sectional view of the apparatus 100 depicted in FIG. 1B taken along lines A-A, according to an example. The substantially symmetrical configuration of the pattern of SES modules 116 and lenses 122 discussed above with respect to FIG. 1B may be more clearly visible in FIG. 1C. For instance, in FIG. 1C, the SES modules 116 are depicted being positioned at approximately 180° around the inner circumference of the perimeter wall 102 from an opposing lens 122.

As also shown in FIG. 1C, an illumination beam 140 may be directed into the hollow core 112 through a lens 112 and onto a SES module 116 positioned substantially directly across from the lens 122. Alternatively, the illumination beam 140 may be directed into the hollow core 112 through any of a plurality of lenses 122 and onto multiple SES modules 116, regardless of the rotational orientation of the apparatus 100. In any regard, emitted light 142, such as Raman scattered light, luminescent light, etc., may be directed out of the hollow core 112 through the lens 122 through which the illumination beam 140 was introduced into the hollow core 112 as shown in FIG. 1C. In addition, or alternatively, the emitted light 142 may be directed out of the hollow core 112 through multiple ones of the lenses 122.

Although not shown in FIG. 1B, another revolution of SES modules 116 and lenses 122 may have a pattern that is opposite the pattern depicted in FIG. 1C. That is, in a next revolution along a longitudinal axis of the perimeter wall 102, lenses 122 may be positioned where the SES modules 116 are depicted as being positioned in FIG. 1C. In this regard, an illumination beam 140 directed onto the perimeter wall 102 from any angle with respect to a rotational direction of the apparatus 100 may be directed through a lens 122 and onto a SES module 116.

According to an example, the lenses 122 focus the illumination beams 140 onto opposing SES modules 116, for instance, as shown by the lines depicted inside the hollow core 112. In this example, the lenses 122 may be convex lenses, and by particular example, the lenses 122 may be microlenses. In another example, the lenses 122 may be transparent components through which light is to pass in a substantially unimpeded manner. In a further example, the lenses 122 may be omitted from the apparatus 100, for instance, as shown in FIG. 1A. In this example, illumination beams 140 and emitted light 142 may enter into and exit from the hollow core 112 through gaps between the SES modules 116 as discussed above. In still further examples, the apparatus 100 may include a combination of the gaps 118 depicted in FIG. 1A and the lenses 122 depicted in FIGS. 1B and 1C.

Turning now to FIG. 1D, there is shown a simplified perspective view of the apparatus 100 depicted in FIGS. 1A and 1B, according to another example. The apparatus 100 depicted in FIG. 1D includes all of the same features as those depicted in FIGS. 1A and 1B and thus, common features will not be described again with respect to FIG. 1D. The apparatus 100 depicted in FIG. 1D differs from the apparatus 100 depicted in FIGS. 1A and 1B in that the SES modules 116 and the lenses 122 are depicted in the apparatus 100 in FIG. 1D as being in a checkered configuration 150. That is, along each height level of the perimeter wall 102, each of the SES modules 116 may be positioned between, i.e., interdigitized with, a pair of lenses 122. In other examples, some or all of the lenses 122 may be omitted and gaps 118 (FIG. 1A) may be provided between some or all of the SES modules 116.

According to an example, the SES modules 116 may be positioned around an inner circumference of the perimeter wall 102 in a spaced arrangement with respect to each other to allow light to enter into the hollow core 112 through the lenses 122 (or gaps 118) between the SES modules 116. Particularly, each of the SES modules 116 may be positioned substantially across from a lens 122 (or gap 118) with respect to the circumference of the perimeter wall 102, such that light passing through a lens 122 (or gap 118) is likely to be directed onto a SES module 116 located across from the lens 122 (or gap 118). In this regard, the apparatus 100 depicted in FIG. 1D may have a similar cross-sectional arrangement as the apparatus 100 depicted in FIG. 1C.

Turning now to FIGS. 2A and 2B, there are shown diagrams of the apparatus 100 respectively depicted in FIGS. 1B and 1D, according to two examples. Particularly, FIGS. 2A and 2B depict the apparatus 100 respectively depicted in FIGS. 1B and 1D, in which the apparatuses 100 may be in substantially flat or uncurled arrangements. As such, a first side end 202 of the apparatuses 100 depicted in FIGS. 2A and 2B may be brought into relatively close proximity to a respective second side end 204 to form the configurations of the apparatuses 100 depicted in FIGS. 1B and 1D. In this regard, the SES modules 116 and the lenses 122 may be positioned with sufficient spacing to enable the perimeter walls 102 to be curled into a cylinder shape.

By way of example, the perimeter wall 102 may be formed of a material and configuration that enables the perimeter wall 102 to have a substantially planar shape and to curl up into a cylinder shape through application or removal of an external stimulus, such as heat, physical pressure, a chemical to react with the perimeter wall 102, etc. The perimeter wall 102 may also be formed of a material and configuration that enables the perimeter wall 102 to retain the curled shape shown in FIGS. 1A-1D following application or removal of the external stimulus. Examples of materials that may be used to form the perimeter wall 102 may include titanium-palladium-nickel, nickel-titanium-copper, gold-cadmium, iron-zinc-copper-aluminium, titanium-niobium-aluminium, uranium-niobium, hafnium-titanium-nickel, iron-manganese-silicon, nickel-titanium, nickel-iron-zinc-aluminium, copper-aluminium-iron, titanium-niobium, zirconium-copper-zinc, nickel-zirconium-titanium, etc.

A particular example of this type of material and configuration may be a shape memory alloy, having a mesh structure in which angles between strands of the mesh structure are to change responsive the amount of heat being applied onto the strands. In this example, a standard configuration of the perimeter wall 102 under normal conditions may be the curled configuration as shown, for instance, FIGS. 1A-1D. When an external stimulus, such as a predetermined amount of heat, is applied onto the perimeter wall 102, the perimeter wall 102 may uncurl to substantially attain the configurations shown in FIGS. 2A and 2B. In addition, when the external stimulus is removed, for instance, the perimeter wall 102 is cooled, the perimeter wall 102 may again become curled as shown in FIGS. 1A-1D.

In addition, or alternatively, the first end 202 may be attached to the second side end 204 through any suitable attachment mechanism. For instance, the first end 202 may be attached to the second side end 204 through use of adhesives, welding, mechanical fasteners, etc. As a further example, the apparatus 100 may be inserted into a transparent sleeve or other ring structure (not shown) to maintain the apparatus 100 in a cylindrical configuration.

As shown in FIG. 2A, the SES modules 116 and the lenses 122 are arranged in a staggered configuration, in which the distances of the SES modules 116 and the lenses 122 from the second end 108 may gradually increase from the first side end 202 to the second side end 204. The angle at which the SES modules 116 and the lenses 122 are staggered may be selected to enable the SES modules 116 and the lenses 122 in subsequent revolutions around the perimeter wall to be increased by one period. In this regard, when the first side end 202 is brought into close proximity to the second side end 204 as shown in FIG. 1B, the SES modules 116 and the lenses 122 may form the double helical configuration 124.

As shown in FIG. 2B, the SES modules 116 and the lenses 122 may be arranged in a checkered configuration with respect to each other. That is, each of the SES modules 116 is depicted as being interdigitized with the lenses 122. In this regard, when the first side end 202 is brought into close proximity to the second side end 204 as shown in FIG. 1D, the SES modules 116 and the lenses 122 may form the checkered configuration 150.

According to an example, and as shown in FIGS. 2A and 2B, the SES modules 116 and the lenses 122 may be positioned on a base layer 210, which is attached to the perimeter wall 102. The base layer 210 may include any of the materials and/or configurations discussed above with respect to the perimeter wall 102. As such, the base layer 210 may include a material and/or a configuration that enables light to pass therethrough. In addition, the base layer 210 may be attached to the perimeter wall 102 through use of adhesives, etc. In one example, the base layer 210 may be formed of a shape memory alloy and configuration to change from a curled to a non-curled configuration through application or removal of a stimulus. In this example, the base layer 210 including the SES modules 116 and the lenses 122 may be caused to have a curled configuration prior to being inserted into the hollow core 112 of a perimeter wall 102.

According to another example, the base layer 210 may be omitted from the apparatus 100 and the SES modules 116 and the lenses 122 may be attached directly onto the perimeter wall 102 through use of, for instance, adhesives. In any regard, the SES modules 116 and the lenses 122 may be fabricated together or separately and positioned together as shown in FIGS. 2A and 2B.

Although FIGS. 2A and 2B have been depicted and described as including lenses 122, it should be understood that the lenses 122 may instead be replaced with gaps 118 without departing from a scope of the apparatus 100 disclosed herein. In this example, for instance, the lenses 122 in the apparatus 100 depicted in FIG. 2A may be omitted to form the apparatus 100 depicted in FIG. 1A.

Figure 3:
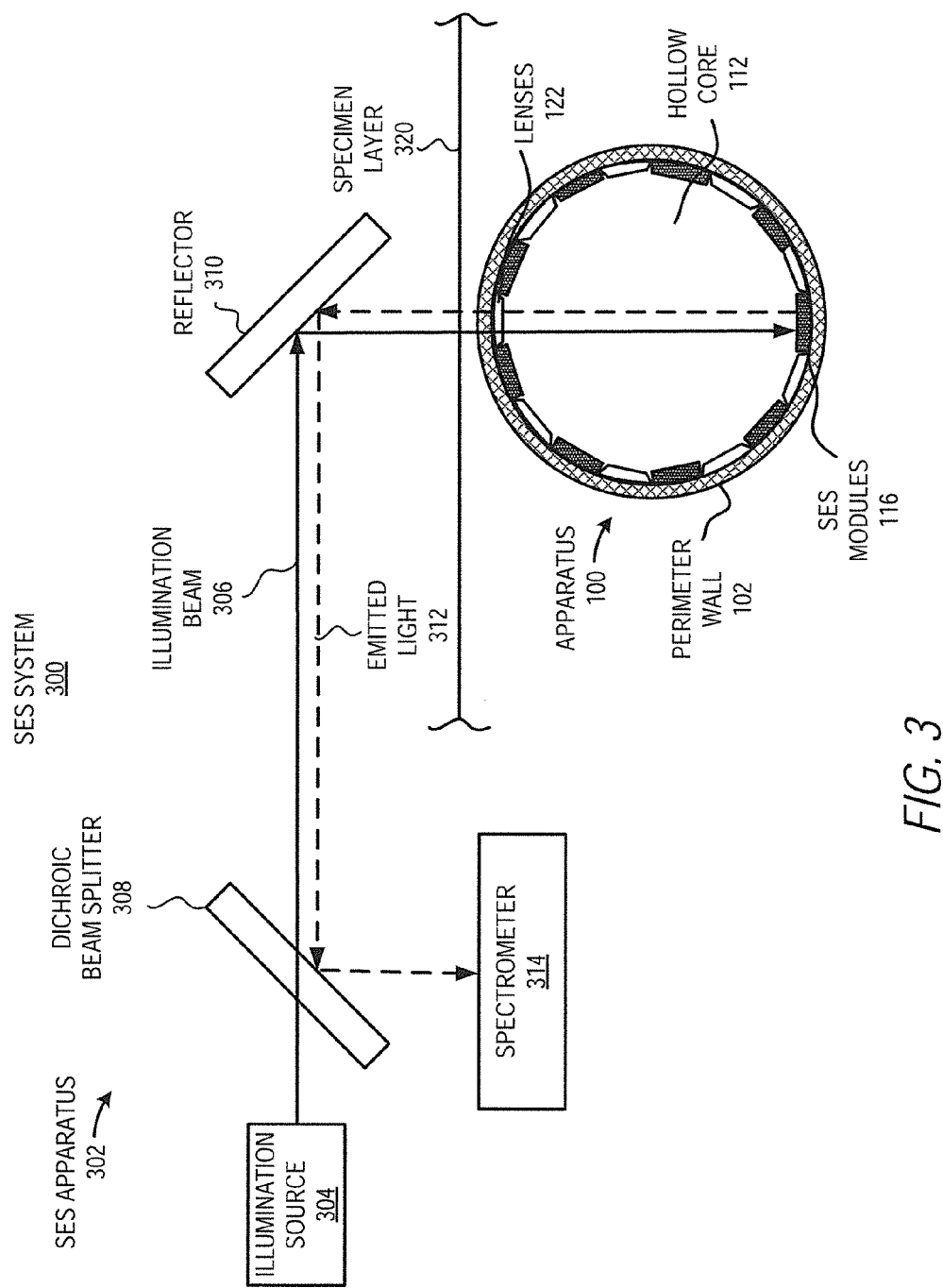
FIG. 3 shows a diagram of a SES system that may include a SES apparatus and an apparatus for performing SES, according to an example of the present disclosure.

Turning now to FIG. 3, there is shown a diagram of a surface-enhanced spectroscopy (SES) system 300 that includes a SES apparatus 302 and an apparatus 100 for performing SES, according to an example. It should be understood that the SES system 300 depicted in FIG. 3 may include additional components and that some of the components described herein may be removed and/or modified without departing from a scope of the SES system 300. It should also be understood that the components depicted in FIG. 3 are not drawn to scale and thus, the components may have different relative sizes with respect to each other than as shown therein.

As shown in FIG. 3, the SES apparatus 302 may include an illumination source 304, which may emit a beam of illumination 306 (such as a laser beam, an LED beam, or other type of light beam) through a dichroic beam splitter 308. The SES apparatus 300 may also include a reflector 310 that is to reflect the illumination beam 306 into the apparatus 100 through a lens 122 to illuminate the SES modules 116 and analyte molecules contained in the hollow core 112 of the apparatus 100. In one regard, because the apparatus 100 may have a substantially symmetrical configuration, the illumination beam 306 is likely to enter into the hollow core 112 regardless of the rotational orientation of the apparatus 100. In other examples, some or all of the lenses 122 may be omitted from the apparatus 100.

Generally speaking, the illumination beam 306 may operate as an excitation light on the SES modules 116, which may cause near fields around the SES modules 116 to be created. The near fields around the SES modules 116 may couple to analyte molecules (not shown) in contact with or in the vicinities of the SES modules 116. The metallic nanoparticles (or other plasmonic structures). of the SES modules 116 may also act to enhance the light emission process of the analyte molecules. As a result, light 312 may be emitted from the analyte molecules and the emission of the light 312 is enhanced by the SES modules 116. A portion of the emitted light 312, which may be emitted in all directions from the analyte molecules near the SES modules 116, may be emitted toward the reflector 310.

According to an example, the SES modules 116 may have substrates (not shown) that are reflective. In this example, the light 312 emitted by the analyte molecules inside of the hollow core 112 may be reflected by the substrates, which may increase the intensity of the emitted light 312 exiting the apparatus 100.

As discussed above, the apparatus 100 may be implanted into a specimen and SES may be performed using the apparatus 100 in vivo. In this regard, the apparatus 100 has been depicted as being implanted underneath a layer 320 of a specimen, which may include, for instance, a skin layer, body tissue, vein walls, cover, etc., under which the apparatus 100 is implanted. In another example, the illumination beam 306 is to pass through a gaseous or liquid environment in which the apparatus 100 has been positioned. In addition, the emitted light 312 is to pass through the surface layer and/or the gaseous or liquid environment.

The illumination beam 306 may therefore pass through the specimen layer 320 prior to entering into the apparatus 100. In addition, the emitted light 312 exiting the apparatus 100 may pass back through the specimen layer 320 and onto the reflector 310. The emitted light 312 may be reflected from the reflector 310 and back to the dichroic beam splitter 308. The dichroic beam splitter 308 may also reflect the emitted light 312 toward a spectrometer 314. The spectrometer 314 may include optical elements, such as, slits, gratings, lenses, etc., that allow for the separation and measurement of different wavelengths of light. The spectrometer 314 may also include a detector, e.g., a photomultiplier tube (PMT), a charge-coupled device (CCD), a complementary metal-oxide-semiconductor (CMOS), etc., detector) to measure the intensities of the separated wavelength bands. The measured intensities of the separated wavelength bands may be used to identify the analyte.

Various modifications may be made to the SES apparatus 302 depicted in FIG. 3 without departing from a scope of the SES system 300. For instance, the reflector 310 may have a parabolic shape that is to focus the illumination beam 306 into the hollow core 112 of the perimeter wall 102 and/or to focus the emitted light 312 onto the dichroic beam splitter 308. As a yet further example, various additional optical components, e.g., mirrors, prisms, optical fibers, etc., may be positioned to direct the illumination beam 306 into the apparatus 100 and/or the emitted light 312 to the spectrometer 314.

Figure 4A:
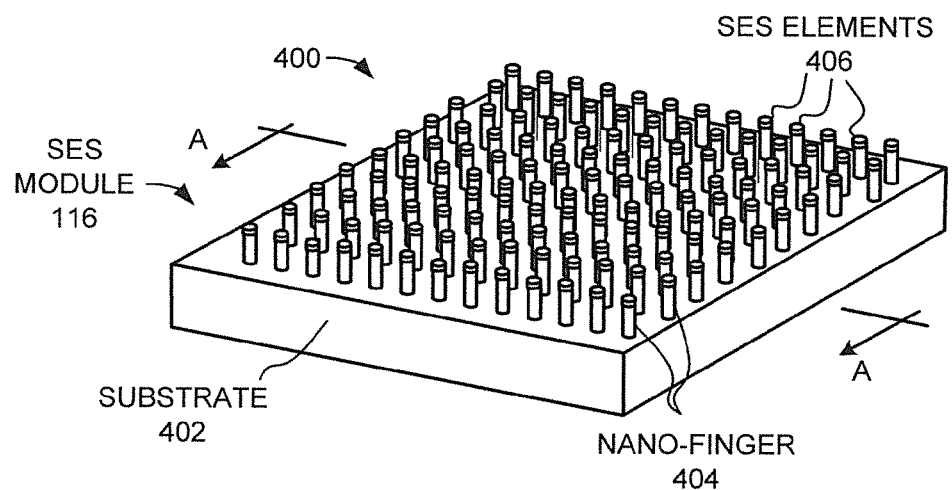
FIG. 4A shows an isometric view of an array of SES modules, in this instance nano-fingers, that may be implemented in the apparatus depicted in FIGS. 1A-3, according to an example of the present disclosure.
Figure 4B:
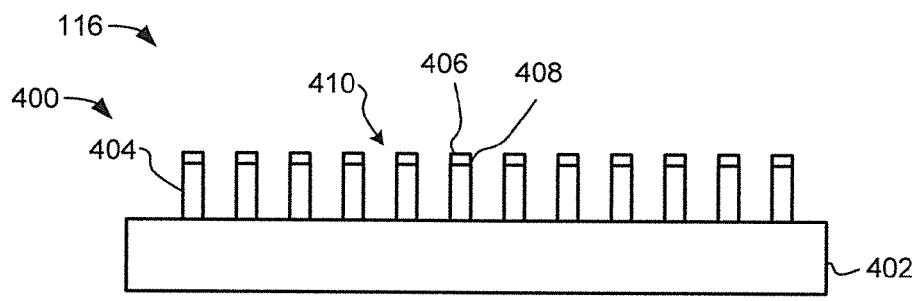
FIGS. 4B and 4C, respectively show cross-sectional views along a line A-A, shown in FIG. 4A, prior to and following collapse of the nano-fingers, according to examples of the present disclosure.
Figure 4C:
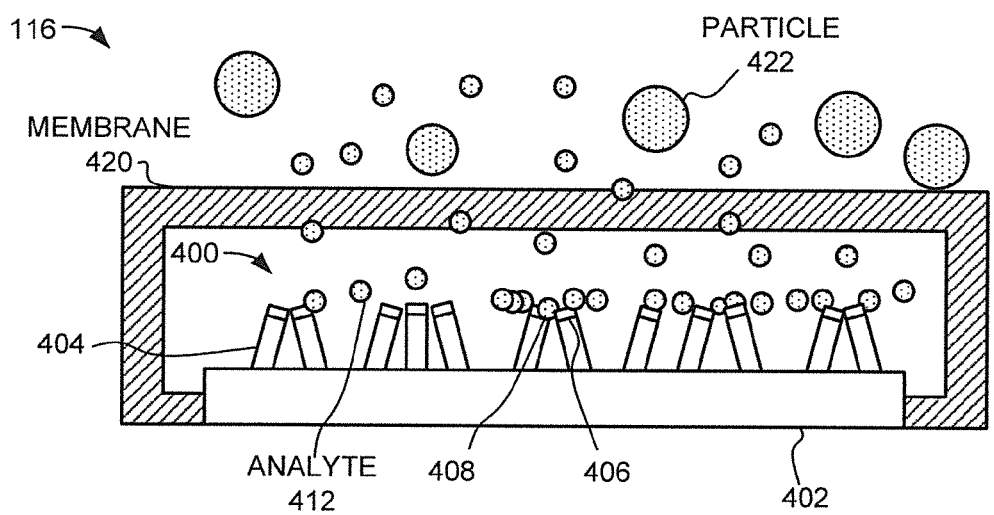

Turning now to FIGS. 4A-4C, there are respectively shown an isometric view and side views of SES module 116, according to an example. It should be understood that the array 400 depicted in FIGS. 4A-4C may include additional components and that some of the components described herein may be removed and/or modified without departing from a scope of the apparatus 100 disclosed herein. It should also be understood that the components depicted in FIGS. 4A-4C are not drawn to scale and thus, the components may have different relative sizes with respect to each than as shown therein.

Generally speaking, the SES module 116 depicted in FIGS. 4A-4C may be an example of a SES module 116, in which SES elements 406 are positioned on the tops of nano-fingers 404 in an array 400. As shown in FIG. 4A, the SES module 116 may include a substrate 402 upon which the nano-fingers 404 may extend. More particularly, the nano-fingers 404 may be attached to and extend above a surface of the substrate 402. The substrate 402 may be formed of any suitable material, such as, silicon, silicon nitride, glass, plastic, polymer, $SiO_2$, $Al_2O_3$, aluminum, etc., or a combination of these materials, etc. In addition, the substrate 402 may include a reflective surface.

According to an example, the nano-fingers 404 may have dimensions that are in the nanometer range, for instance, dimensions that may be less than about 500 nm, and may be formed of a relatively flexible material to enable the nano-fingers 404 to be laterally bendable or collapsible, for instance, to enable tips of the nano-fingers 404 to move toward each other, as discussed in greater detail herein below. Examples of suitable materials for the nano-fingers 404 may include polymer materials, such as, UV-curable or thermal curable imprinting resist, polyalkylacrylate, polysiloxane, polydimethylsiloxane (PDMS) elastomer, polyimide, polyethylene, polypropelene, polyurethane, fluoropolymer, etc., or any combination thereof, metallic materials, such as, gold, silver, aluminum, etc., semiconductor materials, etc., and combinations thereof.

The nano-fingers 404 may be attached to the surface of the substrate 402 through any suitable attachment mechanism. For instance, the nano-fingers 404 may be grown directly on the substrate 402 surface through use of various suitable nano-structure growing techniques. As another example, the nano-fingers 404 may be integrally formed with the substrate 402. In this example, for instance, a portion of the material from which the substrate 402 is fabricated may be etched or otherwise processed to form the nano-fingers 404. In a further example, a separate layer of material may be adhered to the substrate 402 surface and the separate layer of material may be etched or otherwise processed to form the nano-fingers 404. In various examples, the nano-fingers 404 may be fabricated through a nanoimprinting or embossing process in which a template of relatively rigid pillars is employed in a multi-step imprinting process on a polymer matrix to form the nano-fingers 404. In these examples, a template may be formed through photolithography or other advanced lithography with the desired patterning to arrange the nano-fingers 404 in the predetermined arrangement. More particularly, for instance, the desired patterns may be designed on a mold by any of E-beam lithography, photolithography, laser interference lithography, Focused Ion Beam (FIB), self-assembly of spheres, etc. In addition, the pattern may be transferred onto another substrate, for instance, a silicon, glass, or polymer substrate (PDMS, polyimide, polycarbonate, etc.). Various other processes, such as, etching, and various techniques used in the fabrication of micro-electromechanical systems (MEMS) and nano-electromechanical systems (NEMS) may also be used to fabricate the nano-fingers 404.

The nano-fingers 404 have been depicted as having substantially cylindrical cross-sections. It should, however, be understood that the nano-fingers 404 may have other shaped cross-sections, such as, for instance, rectangular, square, triangular, etc. In addition, or alternatively, the nano-fingers 404 may be formed with features, such as, notches, bulges, etc., to substantially cause the nano-fingers 404 to be inclined to collapse in particular directions. Thus, for instance, two or more adjacent nano-fingers 404 may include the features to increase the likelihood that the nano-fingers 404 collapse toward each other. Various manners in which the nano-fingers 404 may be collapsed are described in greater detail herein below.

The array 400 may include a substantially random distribution of nano-fingers 404 or a predetermined configuration of nano-fingers 404. In any regard, according to an example, the nano-fingers 404 may be arranged with respect to each other such that the tips of at least two neighboring nano-fingers 404 are able to be brought into close proximity with each other when the nano-fingers 404 are in a partially collapsed state. By way of particular example, the neighboring nano-fingers 404 may be positioned less than about 100 nanometers apart from each other. According to a particular example, the nano-fingers 404 may be patterned on the substrate 402 such that neighboring ones of the nano-fingers 404 preferentially collapse into predefined geometries, for instance, triangles, squares, pentagons, etc.

In addition, although FIG. 4A depicts the array 400 as having a relatively large number of nano-fingers 404 arranged along each row, it should be understood that the array 400 may include any number of nano-fingers 404 in each row. In one regard, a relatively large number of nano-fingers 404 is provided on the substrate 402 to generally enhance the likelihood of detectable light emissions from molecules of an analyte.

The SES elements 406 may include a plasmonic material such as, but not limited to, gold, silver, copper, platinum, aluminum, etc., or a combination of these metals in the form of alloys, or other suitable material that is able to support surface plasmons for field enhancement for light emissions, such as Raman scattering, luminescence, fluorescence, etc. In addition, the SES elements 406 may be multilayer structures, for example, 10 to 100 nm silver layer with 1 to 50 nm gold over-coating, or vice versa. By definition herein, a plasmonic material is a material that supports plasmons. The SES elements 406 may also include other nanostructures and nanoparticles that are coated with a plasmonic material such as metal. In these examples, the SES elements 406 may include, for instance, gold and silver colloidal nanoparticles, black silicon coated with Au or Ag, etc.

Turning now to FIG. 4B, there is shown a cross-sectional view along a line A-A, shown in FIG. 4A, of the array 400, in accordance with an example. As shown therein, each of the tips 408 of the nano-fingers 404 may include a respective SES element 406 disposed thereon. The SES elements 406, which may include metallic nanoparticles, may be deposited onto the tips 408 of the nano-fingers 404 through one of, for instance, physical vapor deposition (PVD), chemical vapor deposition (CVD), sputtering, etc., of metallic material, or self-assembly of pre-synthesized nano-particles.

Although the nano-fingers 404 have been depicted in FIGS. 4A-4B as each extending vertically and at the same heights with respect to each other, it should be understood that some of the nano-fingers 404 may extend at various angles and heights with respect to each other. The differences in angles and/or heights between the nano-fingers 404 may occur, for instance, due to differences arising from manufacturing or growth variances existent in the fabrication of the nano-fingers 404 and the deposition of the SES elements 406 on the nano-fingers 404, etc.

As shown in FIG. 4B, the nano-fingers 404 are in a first position, in which the tips 408 may be in a substantially spaced arrangement with respect to each other. The gaps 410 between the tips 408 may be of sufficiently large size to enable a liquid to be positioned in the gaps 410. In addition, the gaps 410 may be of sufficiently small size to enable the tips 408 of at least some of the nano-fingers 404 to be drawn toward each other as the liquid provided in the gaps 410 evaporates, through, for instance, capillary forces applied on the tips 408 as the liquid evaporates.

Turning now to FIG. 4C, there is shown a cross-sectional view along a line A-A, shown in FIG. 4A, of the array 400, following evaporation of the liquid, according to an example. The view depicted in FIG. 4C is identical to the view depicted in FIG. 4B, except that the nano-fingers 404 are depicted in a second position, in which the tips 408 of some of the nano-fingers 404 have been drawn toward with each other. According to an example, the tips 408 of some of the nano-fingers 404 may be in and may remain in relatively close proximities to each other for a period of time due to the capillary forces applied on adjacent ones of the nano-fingers 404 during and following evaporation of the liquid (not shown) in the gaps 410 between the tips 408. In addition, the SES elements 406 on the adjacent tips 408 may bond to each other through, for instance, gold-gold bonding, a binding molecule (not shown), etc.

When an illumination source emits an excitation light (or equivalently, a pump light), such as a laser beam, an LED beam, etc., onto the SES elements 406, the SES elements 406 may create near fields around the SES elements 406. The near fields around the SES elements 406 may couple to analyte molecules 412 in the vicinities of the SES elements 406. The metallic nanoparticles (or other plasmonic structures) of the SES elements 406 may also act to enhance the emission process of the analyte molecules 412. As a result, light 312 is emitted from the analyte molecules 412 and the emission of the light 312 is enhanced by the SES elements 406.

In any event, and in one regard, the tips 408 of the nano-fingers 404 may be caused to be drawn toward each other as shown in FIG. 4C to enhance light emissions by the analyte molecules 412 in the near fields of the SES elements 406 because the relatively small or no gaps between the SES elements 406 on the adjacent tips 408 may create "hot spots" having relatively large electric field strengths. According to an example, the nano-fingers 404 may be positioned into the partially collapsed state depicted in FIG. 4C prior to insertion of the apparatus 100 into a specimen. In this regard, the nano-fingers 404 may be positioned into the partially collapsed state prior to, during, or after attachment of the SES module 116 onto the perimeter wall 102 of the apparatus 100.

According to an example, the SES module 116 depicted in FIGS. 4A-4C may include the substrate 402 and may be inserted into the apparatus 100. For instance, the substrate 402 of the SES module 116 may be attached to interior surface of the perimeter wall 102 through use of an adhesive.

As also shown in FIG. 4C, the SES module 116 may also include a partially-permeable exchange membrane 420 that substantially encases the nano-fingers 404 and the SES elements 406. In one regard, the partially-permeable exchange membrane 420 may be formed a material and/or configuration that enables target analyte molecules 412 to pass therethrough while substantially blocking larger particles 422 from passing therethrough. As such, for instance, the partially-permeable exchange membrane 420 may substantially protect the nano-fingers 404 and the SES elements 406 from damage and/or blockage by the larger particles 422 that may be found in a fluid flow stream. By way of example, the partially-permeable exchange membrane 420 may be formed of any of the materials and configurations discussed above with respect to the porous membrane 130.

According to another example, the SES module 116 may have the SES elements 406 without the nano-fingers 404. In this example, the SES elements 406 may be deposited and/or formed directly on the substrate 402. In addition, or alternatively, the SES elements 406 may initially be formed and positioned, for instance, as shown in FIG. 4C, such that the SES elements 406 are either touching each other or are in relatively close proximities to each other and the SES elements 406 may be transferred to another substrate, in which the another substrate and the SES elements 406 form a SES module 116.

Figure 5:
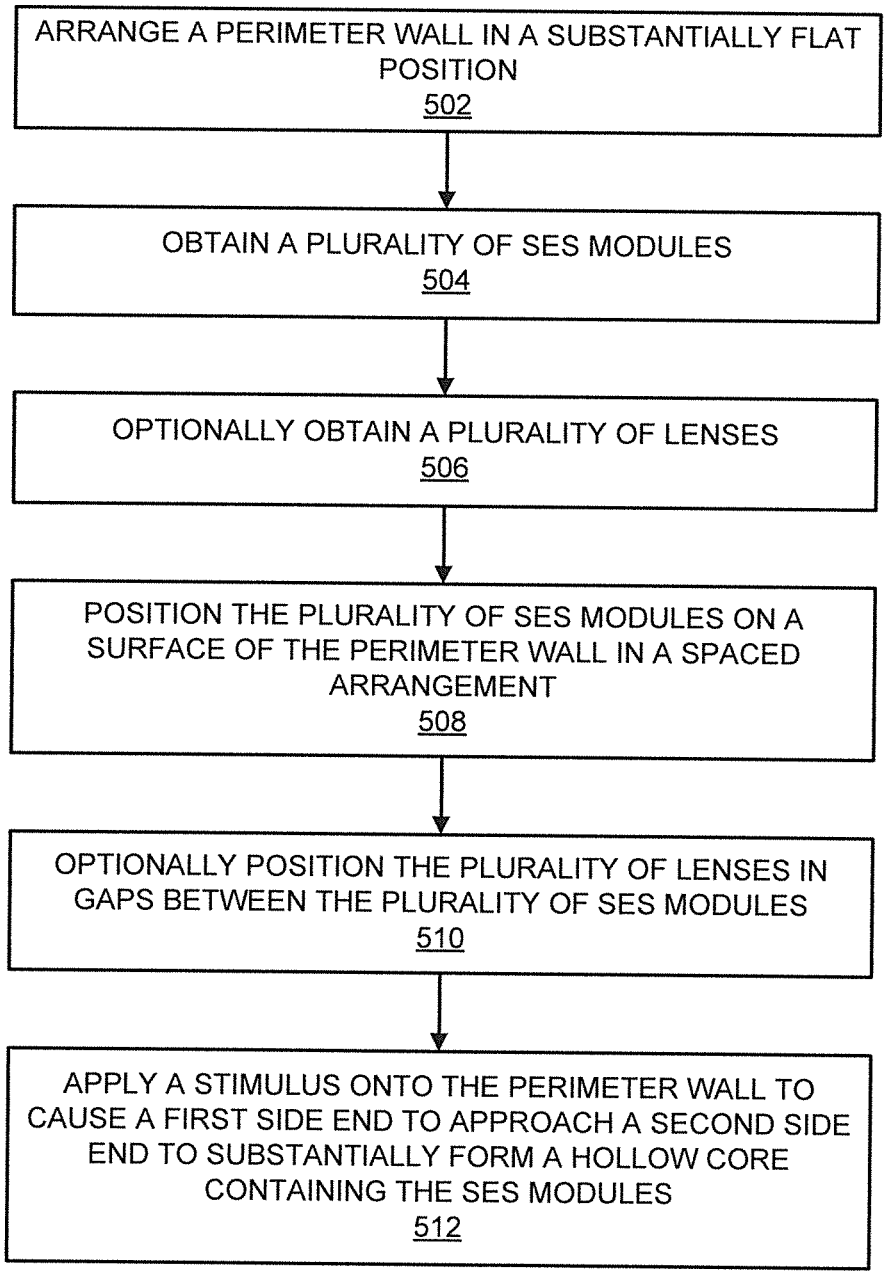
FIG. 5 shows a flow diagram of a method for fabricating an apparatus for performing spectroscopy, according to an example of the present disclosure.

Turning now to FIG. 5, there is shown a flow diagram of a method 500 for fabricating an apparatus 100 for performing spectroscopy, according to an example. It should be understood that the method 500 depicted in FIG. 5 may include additional processes and that some of the processes described herein may be removed and/or modified without departing from a scope of the method 500. In addition, although particular reference is made herein to the apparatus 100 as being fabricated through implementation of the method 500, it should be understood that the method 500 may be implemented to fabricate a differently configured apparatus without departing from a scope of the method 500.

At block 502, a perimeter wall 102 may be arranged in a substantially flat position. As shown in FIGS. 2A and 2B, the perimeter wall 102 may include a first side end 202 and a second side end 204, in which the second side end 204 may oppose the first side end 202. In addition, as discussed above, the perimeter wall 102 may be formed of a material and/or a configuration that enables light to pass through the perimeter wall 102. Particularly, the perimeter wall 102 may be formed of a material and/or a configuration that enables a sufficient intensity of an illumination beam 140, 306 to pass through the perimeter wall 102 for light 312 to be emitted from analyte molecules contained inside of the apparatus 100 formed by the perimeter wall 102 and for the emitted light 312 to be of sufficient intensity to be detected.

At block 504, a plurality of SES modules 116 may be obtained. Each of the SES modules 116 may include a substrate 402 and a plurality of SES elements 406 discussed above with respect to FIGS. 4A-4C. In any regard, the SES modules 116 may be obtained through fabrication of the SES modules 116 in any of the manners discussed above. According to a particular example, the SES modules 116 may include the SES elements 406 provided on the tips 408 of nano-fingers 406, as shown in FIG. 4C. In other examples, the SES modules 116 may include substrates on which the SES elements 406 have been directly provided. The SES modules 116 may also include the partially-permeable exchange membrane 420 discussed above with respect to FIG. 4C.

At block 506, a plurality of lenses 122 may optionally be obtained. The obtaining of the lenses 122 may be considered to be optional because the apparatus 100 disclosed herein may be implemented without the lenses 122 in some examples as discussed above. In any regard, the lenses 122, if obtained, may be any of the lenses 122 discussed above. According to an example, the obtaining of the lenses 122 at block 506 may include fabricating the lenses to have dimensions similar to the dimensions of the SES modules 116. In addition, or alternatively, the lenses 122 may be pre-fabricated and may thus be obtained from a manufacturer and/or supplier of the lenses 122.

At block 508, the SES modules 116 may be positioned on a surface of the perimeter wall 102 in a spaced arrangement with respect to each other. According to two examples, the SES modules 116 may be positioned on the surface of the perimeter wall 102 in the manners depicted in FIGS. 2A and 2B.

At block 510, the plurality of lenses 122, if obtained, may optionally be positioned in a plurality of gaps 118 between the SES modules 116. According to two examples, the lenses 122 may be positioned on the surface of the perimeter wall 102 in the manners depicted in FIGS. 2A and 2B.

At block 512, a stimulus may be applied onto and/or removed from the perimeter wall 102 to cause a first side end 202 to approach a second side end 204 to substantially form a hollow core 112 containing the SES modules 116. The stimulus may include, for instance, heat, physical pressure, a chemical to interact with the perimeter wall 102, etc. The application of the stimulus may also include the removal of heat, e.g., cooling, of the perimeter wall 102. In addition, the first side end 202 may be attached or held in relatively close proximity to the second side end 204 to maintain the hollow core 112 shape in any of the manners discussed above with respect to FIGS. 2A and 2B. Following block 512, an apparatus 100 as depicted in any of FIGS. 1A-1D may be fabricated.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. An apparatus for performing spectroscopy comprising:
    a perimeter wall extending between a first end and a second end of the perimeter wall along a first axis, wherein an interior surface of the perimeter wall forms a hollow core extending along the first axis, wherein the perimeter wall has openings at both the first end and the second end, and wherein light is to pass to through the perimeter wall; and
    a plurality of surface-enhanced spectroscopy (SES) modules positioned around an inner circumference of the perimeter wall in a spaced arrangement with respect to each other to allow light to enter into the hollow core in gaps between the plurality of SES modules, and wherein each of the plurality of SES modules is positioned substantially across from a gap.

2. The apparatus according to claim 1, wherein the plurality of SES modules are positioned in a pattern that is substantially symmetrical about multiple planes along a central longitudinal axis of the hollow core.

3. The apparatus according to claim 1, wherein the plurality of SES modules are positioned in a helical configuration along the inner surface of the perimeter wall in a direction from the first end to the second end.

4. The apparatus according to claim 1, further comprising:
    a plurality of lenses positioned in a plurality of the gaps between the plurality of SES modules.

5. The apparatus according to claim 4, wherein the plurality of lenses are to focus light entering into the perimeter wall onto the SES modules.

6. The apparatus according to claim 4, wherein the plurality of lenses and the plurality of SES modules are positioned around the entire inner circumference of the cylindrical housing.

7. The apparatus according to claim 4, wherein the plurality lenses and the plurality of SES modules are arranged in a double helical configuration along the to inner surface of the perimeter wall in a direction from the first end to the second end.

8. The apparatus according to claim 4, wherein the plurality of lenses and the plurality of SES modules are arranged in a pattern in which the plurality of lenses is are positioned between pairs of SES modules along a second axis that is perpendicular to the first axis.

9. The apparatus according to claim 1, further comprising:
    a porous membrane covering at least one of the openings at the first end and the second end, wherein the porous membrane is to filter a fluid entering into the hollow core.

10. The apparatus according to claim 1, wherein each of the plurality of SES modules comprises a substrate and SES elements provided on the substrate.

11. The apparatus according to claim 10, wherein each of the plurality of SES modules further comprises a plurality of nano-fingers extending from the substrate, wherein the Raman-enhancing elements are attached to tips of the plurality of nano-fingers.

12. The apparatus according to claim 10, wherein the plurality of SES modules comprise a partially-permeable exchange membrane that substantially encases the SES elements, wherein the partially-permeable exchange membrane is to protect the SES elements while allowing target analyte molecules to pass through the partially-permeable exchange membrane.

13. A system for performing surface-enhanced spectroscopy (SES), said apparatus comprising:
an apparatus having,
a perimeter wall extending between a first end and a second end of the perimeter wall along a first axis, wherein an interior surface of the perimeter wall forms a hollow core extending along the first axis, wherein the perimeter wall has openings at both the first end and the second end, and wherein light is to pass through the perimeter wall; and
a plurality of surface-enhanced spectroscopy (SES) elements positioned around an inner circumference of the perimeter wall in a spaced arrangement with respect to each other to allow light to enter into the hollow core in gaps between the plurality of SES modules, wherein each of the plurality of SES modules is positioned substantially across from a gap, such that light passing through a gap is likely to be directed onto a SES module located across from the gap, and wherein the plurality of SES modules are positioned in a pattern that is substantially symmetrical about multiple planes along a central longitudinal axis of the perimeter wall;
an illumination source to illuminate the plurality of SES modules; and
a spectrometer positioned to detect light emitted from an analyte positioned near the plurality of SES modules.

14. The system according to claim 13, wherein the apparatus further comprises a plurality of lenses positioned in a plurality of the gaps between the plurality of SES modules.

15. The system according to claim 13, wherein the plurality of SES modules comprises a partially-permeable exchange membrane that substantially encases the SES elements, wherein the partially-permeable exchange membrane is to protect the SES elements while allowing target analyte molecules to pass through the partially-permeable exchange membrane.

16. A method for fabricating an apparatus, the method comprising:
arranging a perimeter wall in a substantially flat position, said perimeter wall having a first side end and a second side end that opposes the first side end, and wherein light is to pass through the perimeter wall;
positioning a plurality of surface-enhanced spectroscopy (SES) modules on a surface of the perimeter wall in a spaced arrangement with respect to each other, each of the plurality of SES modules comprising a plurality of SES elements; and
applying a stimulus onto the perimeter wall to cause the first side end to approach the second side end to substantially form a hollow core containing the plurality of SES modules, wherein the plurality of SES modules are positioned on the surface of the perimeter wall in an arrangement that enables light to enter into the hollow core through gaps between the plurality of SES modules and such that each of the plurality of SES modules is positioned substantially across from a gap between the plurality of SES modules.

17. The method according to claim 16, further comprising:
positioning a plurality of lenses in the gaps between the plurality of SES modules.

18. The method according to claim 17, further comprising:
positioning the plurality of SES modules and the plurality of lenses on the perimeter in an arrangement that results in a double helical configuration along the inner surface of the perimeter wall in a direction from a first end to a second end of the perimeter wall when the first side end is caused to approach the second side end to substantially form a hollow core.

19. The method according to claim 16, wherein following formation of the hollow core, the perimeter wall has openings at both a first end and a second end of the perimeter wall, said method further comprising:
covering at least one of the openings with a porous membrane that is to filter a fluid entering into the hollow core.

20. The method according to claim 16, further comprising:
providing each of the plurality of SES modules with a partially-permeable exchange membrane that substantially encases the SES elements, wherein the partially-permeable exchange membrane is to protect the SES elements while allowing target analyte molecules to pass through the partially-permeable exchange membrane.

* * * * *